(12) United States Patent
Kessler et al.

(10) Patent No.: US 7,311,816 B2
(45) Date of Patent: Dec. 25, 2007

(54) DEVICE FOR DETERMINING THE RESIDUAL LIQUID CONTENT OF SOLIDS CAKES IN CENTRIFUGES

(75) Inventors: Ruth Kessler, Leverkusen (DE); Karl Helmut Berg, Bergisch Gladbach (DE); Karl-Gustav Pattberg, Erftstadt (DE); Werner Dick, Leverkusen (DE)

(73) Assignee: Bayer Technology Services GmbH, Leverkusen (DE)

( * ) Notice: Subject to any disclaimer, the term of this patent is extended or adjusted under 35 U.S.C. 154(b) by 393 days.

(21) Appl. No.: 10/494,426

(22) PCT Filed: Oct. 17, 2002

(86) PCT No.: PCT/EP02/11619

§ 371 (c)(1),
(2), (4) Date: Apr. 27, 2004

(87) PCT Pub. No.: WO03/037522

PCT Pub. Date: May 8, 2003

(65) Prior Publication Data

US 2005/0000869 A1 Jan. 6, 2005

(30) Foreign Application Priority Data

Oct. 29, 2001 (DE) ................................ 101 53 353

(51) Int. Cl.
*B04B 13/00* (2006.01)

(52) U.S. Cl. .................... 210/85; 210/96.1; 210/360.1; 73/73; 324/689; 324/695

(58) Field of Classification Search ................ 324/689, 324/695; 340/604; 73/73–74; 210/85, 96.1, 210/360.1, 402
See application file for complete search history.

(56) References Cited

U.S. PATENT DOCUMENTS

| 2,729,099 A | * | 1/1956 | Rosenthal | ...................... 73/73 |
| 3,686,606 A | | 8/1972 | Thoma | ......................... 338/35 |
| 3,815,745 A | * | 6/1974 | Bondarev et al. | .......... 210/96.1 |
| 3,993,243 A | * | 11/1976 | Dietzel et al. | ................. 494/36 |
| 6,063,292 A | * | 5/2000 | Leung | ......................... 210/739 |

FOREIGN PATENT DOCUMENTS

| CH | 640 352 | 12/1983 |
| DE | 36 15 013 | 6/1987 |
| DE | 197 16 128 | 2/1999 |
| EP | 0 891 814 A2 | 1/1999 |
| WO | WO 00/16081 | 3/2000 |

* cited by examiner

*Primary Examiner*—Terry K Cecil
(74) *Attorney, Agent, or Firm*—Norris, McLaughlin & Marcus PA

(57) ABSTRACT

A device for determining the residual liquid content of solids cakes in a centrifuge basket. The device includes two electrodes protruding through a wall of the basket and into the solids cake; a conductivity or capacitance measuring device (13) measuring the conductivity of the solids cake between the electrodes; and evaluation and control units contactlessly receiving data from the measuring device to affect the operation of the centrifuge.

15 Claims, 3 Drawing Sheets

DEVICE FOR DETERMINING THE RESIDUAL LIQUID CONTENT OF SOLIDS CAKES IN CENTRIFUGES

This is a 371 of PCT/EP02/11619 filed 17 Oct. 2002 (international filing date).

The invention relates to a device for measured value acquisition, processing and transmission in centrifuges for the separation of liquids and solids, in particular skimming centrifuges.

BACKGROUND OF THE INVENTION

Skimming centrifuges with vertically or horizontally driven baskets are known. It is also known that, in the case of poorly flowing moist solids, the solids discharge takes place by means of screws instead of by means of chutes.

There are known methods, specifically ultrasonic and infrared measuring methods, which determine the degree of residual moisture of the solids cake in a skimming centrifuge during the dewatering operation by means of contactless measurement. The reflection of the pulses takes place on the surface of the filling, so that only the degree of residual moisture of the surface of the filling is determined.

With ultrasound, measurement is carried out, for example according to DE-A-19 716 128, in such a way that the echo delay of an ultrasound pulse between the ultrasound transmitter, the impinged surface of the filling and the ultrasound receiver is measured and the degree of residual moisture is determined by the evaluation of the quality of the echo of a reflected ultrasound pulse. Measuring errors are caused by differences in the nature of the surface, vapors, mist and dust.

According to laid-open patent application EP-A-891 814, infrared radiation is used for measuring the degree of moisture by the radiation intensity of a light pulse which is reflected from the surface of the filling being measured and the degree of residual moisture being determined by the evaluation of the change in the radiation intensity. Measuring errors are caused here by differences in the nature of the surface and by differences in the color of the filling medium.

It has until now been necessary for a skimming centrifuge to be operated on the basis of empirical values, according to which it is assumed that the solids cake has reached a specific residual moisture after a specific dewatering period, whereupon further working steps can then be carried out, such as for example the skimming discharge of the solids cake. In the case of these empirical values, however, it is necessary to take into account different filtration rates, which are produced for example when there are differently compacted base layers or different suspension characteristics, in particular solids size distribution.

After centrifuging off surplus liquid as a filtrate, the remaining solids cake is dewatered, the degree of residual moisture depending on the dewatering kinetics. The degree of residual moisture varies over the height of the solids cake. The layer of the solids cake that is nearest the basket shell, varying in its height and dependent on the filling medium, is saturated with liquid. The layer of the solids cake lying over that is saturated at the beginning of the dewatering operation and has moisture removed to an extent depending on the dewatering kinematics. At any time during the dewatering, the degree of residual moisture at the surface of the filling is less than or equal to that of the remaining solids cake and is not necessarily always in the same relationship with the degree of residual moisture of the remaining solids cake.

The invention is therefore based on the object of designing a device of the type stated at the beginning in such a way that the degree of residual moisture can be determined in a way in which the product is contacted and the measurement takes place continuously during the dewatering operation and over the entire height of the solids cake or a large proportion of the height of the solids cake, in order to be able to restrict the operating times of the solids-liquid separating device to the amount necessary in each case.

SUMMARY OF THE INVENTION

This object is achieved by a device for determining the residual moisture content of solids cakes in centrifuges which at least comprises at least two sensors, in particular electrodes, and a measuring device which is connected to the sensors and is provided for measuring the residual moisture, in particular a conductivity or capacitance measuring device, the sensors being arranged spaced apart from one another in the region of the centrifuge basket.

DETAILED DESCRIPTION

The sensors are preferably provided in the edge of the basket. Consequently, it is possible for the dewatering over the cross section of the solids cake to be monitored.

Furthermore, the measuring device is preferably provided in the edge of the basket.

The sensors are particularly preferably electrodes of a material selected from the series: corrosion-resistant steel, platinum, gold, nickel and copper. Since the electrodes are contacted by the product, chemically inert materials are preferred.

In a preferred configuration, the measuring device is connected to a telemetry unit, which transmits measuring data contactlessly from the centrifuge basket to the outside.

Most particularly preferred is a variant of the device in which the telemetry unit contains a transmitter, arranged opposite which in the region of the centrifuge housing is a receiver. By this means, contactless data transmission from the centrifuge basket is possible during the operation of the centrifuge.

In a preferred configuration of the device, the receiver is connected to an evaluation unit and a control unit for controlling the operation of the centrifuge.

In a particular form of construction, the measuring device for sensing the moisture is operated by means of an external voltage supply, arranged partly outside the centrifuge basket. A permanent voltage supply and uninterrupted operation is hereby ensured, in particular in the case of a measuring device provided on the rotating basket.

It is particularly preferred for the voltage supply to comprise a high-frequency transmitter with a transmitting coil and an AC/DC converter with a receiver coil, the AC/DC converter being electrically connected to the measuring device on the basket and supplying the possibly required DC voltage for the measuring device.

For protection from corrosion and attack by the solids and liquids treated in the centrifuge, in a further preferred configuration of the device the voltage supply arranged in the region of the centrifuge basket, the measuring device and if appropriate the telemetry unit are arranged such that they are closed from the surroundings in a ring, which consists of a non-metallic material, in particular of glass-fiber reinforced plastic.

A curable plastic, in particular epoxy resin or phenolic resin, is used particularly preferably as the material. The electronic components on the basket are embedded in this material.

It is particularly preferred for an additional supporting ring, which is firmly connected to the edge of the basket, to be provided around the outer circumference of the ring.

The ring, the supporting ring and the transmitting and receiving units may be connected releasably or unreleasably to the centrifuge basket or the centrifuge housing.

The device according to the invention can be used in all centrifuges for the separation of liquids and solids, in particular in skimming centrifuges or in other filtering centrifuges, in particular horizontal filter-bag centrifuges and pendulum centrifuges as well as centrifugal dryers and screen centrifuges, in particular pusher centrifuges and screen-conveyor centrifuges.

Centrifuge dryers are used for the separation of liquids and solids with mechanical and thermal dewatering.

The subject matter of the invention is therefore also a centrifuge, in particular a skimming centrifuge, filtering centrifuge, centrifuge dryer or screen-conveyor centrifuge, having a measuring device according to the invention.

The sensing and interpretation of the resistance or conductivity of the solids cake allows the device according to the invention to be used to determine the following:

The porous filter cake is saturated with liquid (a low resistance or high conductivity is characteristic).

The porous filter cake has been dewatered to a certain extent (an increased resistance is characteristic, the conductivity decreasing nonlinearly, but perceptibly and reproducibility as dewatering progresses).

The device is capable of continuously determining the degree of residual moisture by the evaluation of the conductivity of the solids cake over a filling height of several centimeters. When the desired degree of residual moisture is reached, the solids cake is discharged by means of the skimming device and a new processing cycle is commenced by introducing suspension. The possibility of establishing the degree of residual moisture at the actual time allows the solids cake to be discharged with the respectively desired residual moisture after the minimum possible dewatering period in each case.

Also mentioned as alternative suitable measuring devices for the sensing and interpretation of the degree of residual moisture are measuring units with capacitors for capacitance measurement, which can be integrated in the centrifuge basket in place of the conductivity measuring device.

BRIEF DESCRIPTION OF THE DRAWINGS

The invention is explained in more detail below by way of example on the basis of the figures, in which.

EXAMPLES

Figure 1:
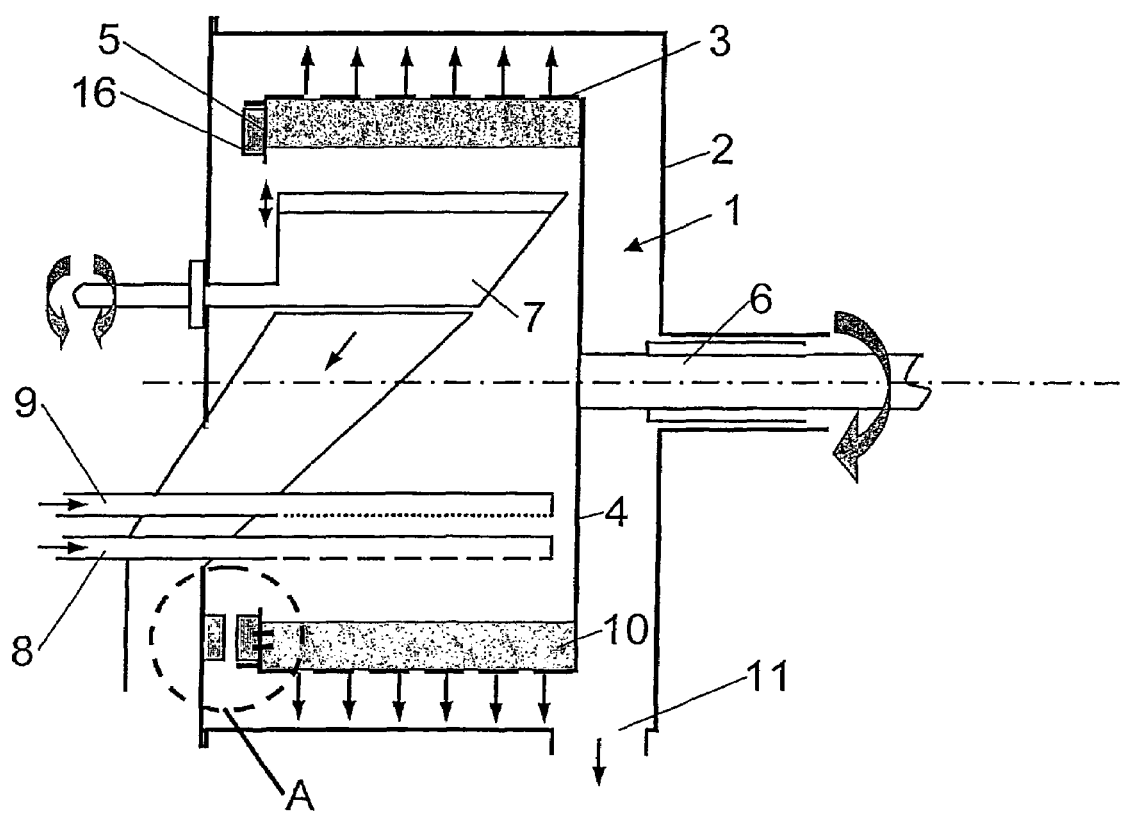
FIG. 1 shows a skimming centrifuge with a measuring device according to the invention in cross section as a diagram.

An exemplary embodiment of a centrifuge in which a device according to the invention is integrated is explained on the basis of FIG. 1, which shows the section through a filter centrifuge in a schematic representation. According to this, a filter basket 1 is mounted in a closed centrifuge housing 2 and is connected to the drive (not shown). The filter basket 1 comprises a basket shell 3, containing a screen area, and also a basket base 4 and a basket edge 5. The basket shaft 6 bears the basket base 4 and is mounted in the centrifuge housing 2. In an alternative form of construction which is not shown, the filter basket 1 has a closed basket shell with a filtrate run-off via the basket base.

Protruding into the filter basket 1 is a skimming device 7, which is pivotably mounted in the centrifuge housing 2. Furthermore, a filling tube 8 for the product suspension and a washing tube 9 for one or more washing liquids-protrude into the filter basket 1.

During the operation of the centrifuge, the suspension introduced into the filter basket 1 via the filling tube 8 is distributed over the basket shell 3 and separates into a solids cake 10 comprising particles of solid matter, and a liquid filtrate. The said filtrate penetrates the solids cake 10, is centrifuged off outward and drained away via the filtrate outlet 11, or in the configuration not shown with a closed basket shell 3 via the basket base 4, out of the centrifuge housing 2. The washing liquid introduced into the filter basket 1 is distributed over the remaining solids cake 10, penetrates the solids cake 10, is centrifuged off outward and drained away via the filter outlet 11 from the centrifuge housing 2. The solids cake 10 is dewatered by centrifuging off the pore liquid for a shorter or longer period of time and discharged at intervals from the filter basket I by means of the skimming device 7.

Figure 2:
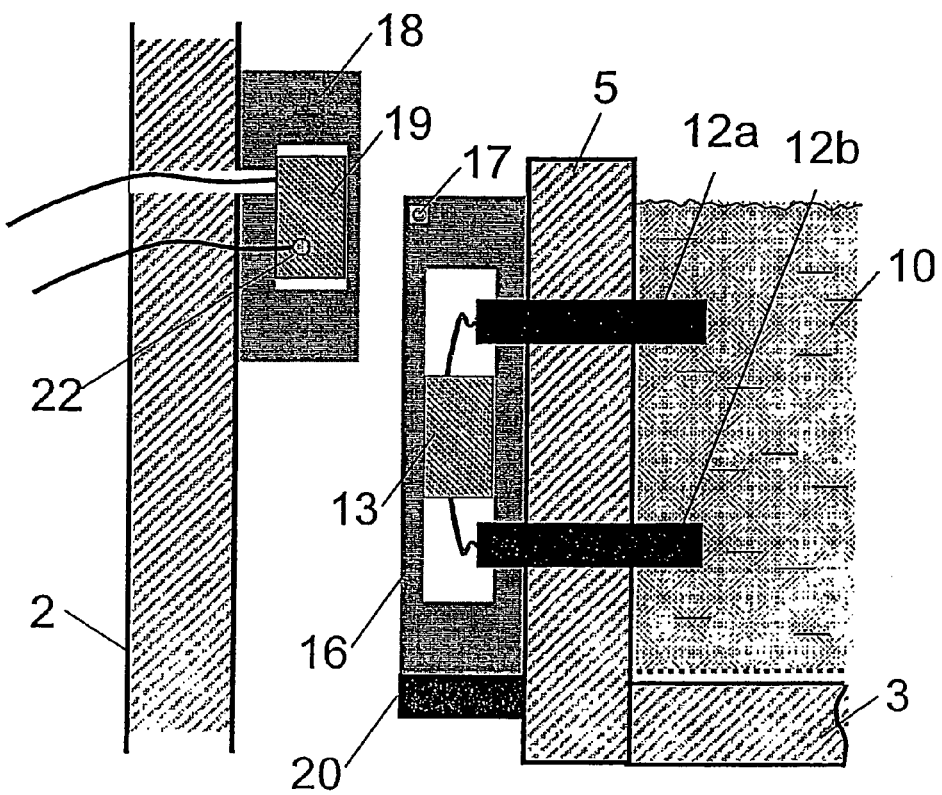
FIG. 2 shows an enlarged detail A from FIG. 1.
Figure 3:
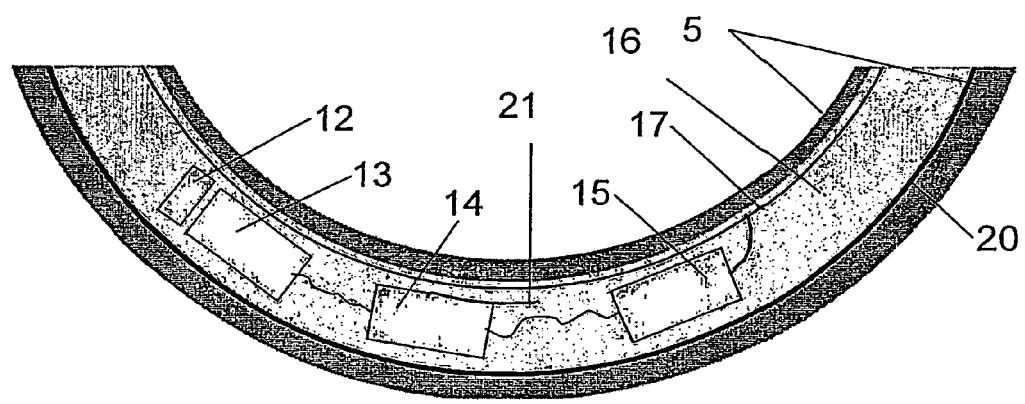
FIG. 3 shows a partial view of the edge of the basket with the measuring device, telemetry and power supply.

The moisture measuring device is a conductivity measuring device, comprising the spatially separate electrodes 12$a$, 12$b$ (shown in FIG. 2), which are fixed to the edge of filter basket 1 and the ends of which protrude into the solids cake 10, and the measuring signal of which is converted in a measuring transducer 13 and fed to a telemetry unit 14 (shown in FIG. 3) operated at high frequency. The devices are supplied with DC voltage via an AC/DC converter 15 (shown in FIG. 3). The components 13 to 15 are integrated in a ring 16 made of phenolic resin reinforced with glass fibers, which is fastened on the edge of the basket 5 and follows the movement of the filter basket 1.

Also integrated in the ring 16 over the circumference is a copper receiving coil 17, via which an AC voltage is induced by a transmitting device 18 which includes a number of copper transmitter coils 19 and is supplied with power via a generator (not shown) being located on the centrifuge housing 2.

To relieve the ring material of centrifugal forces, the ring 16 is surrounded by a steel supporting ring 20 connected to the edge of the basket 5.

For the transmission of the measured signal, the measured value sent by the transmitter antenna 21 of the transmitter of the telemetry unit 14 is received by a receiver 22 and passed on to a measured value unit (PC) not shown here.

In particular if there is inadequate dimensioning of the gap between the outer surface of the edge of the basket 5 and the centrifuge housing 2, the units 16 and 18 may alternatively be integrated in the edge of the basket 5 and the centrifuge housing 2, respectively.

Figure 4:
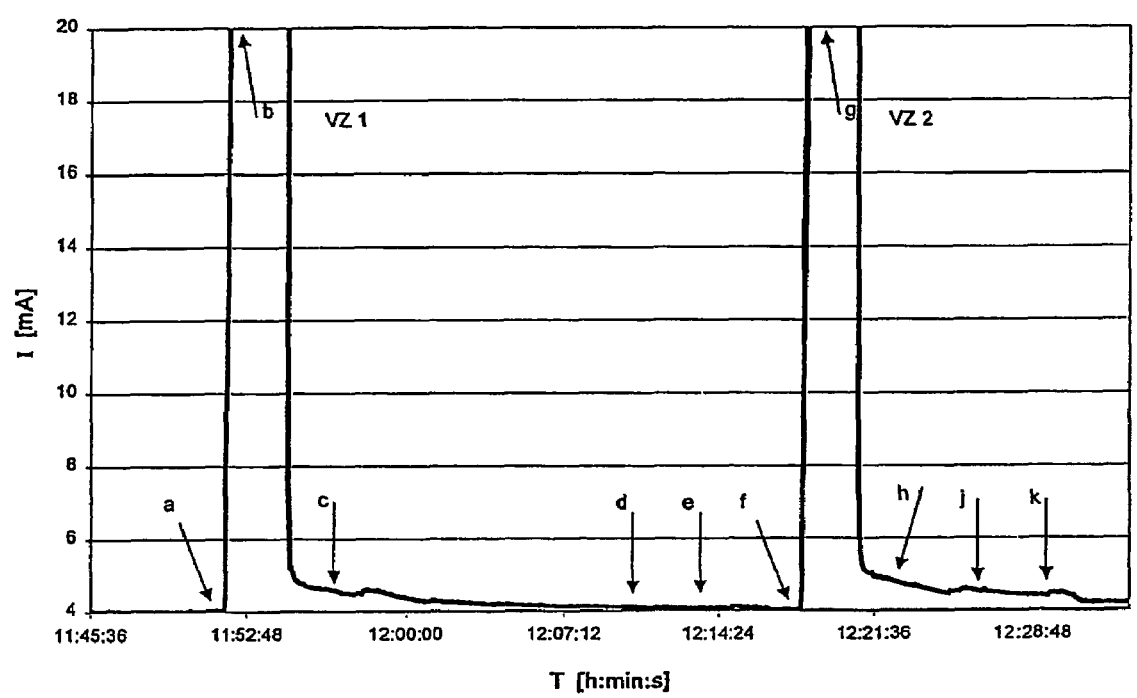
FIG. 4 shows a diagram to explain the processing cycle, in which the current proportional to the conductivity is plotted against time.

An operational test which was carried out with the invention is explained on the basis of a processing cycle diagram (see FIG. 4) of the skimming centrifuge based on the conductivity of the solids cake, and the advantage of the device according to the invention becomes clear.

In the processing cycle VZ1, the suspension is fed to the filter basket 1 in the time period (a) to (b), whereby the conductivity of the solids cake 10 rises to a maximum. The layer of liquid over the solids cake 10 is centrifuged off to the outside and the operation of dewatering the solids cake 10 commences between (b) and (c), with the result that the conductivity clearly drops. At (c), the rotational speed of the filter basket 1 is raised and the dewatering operation is continued until (d), after which the solids cake 10 is discharged by skimming between (d) and (e) and a new processing cycle begins at (f). In the processing cycle VZ2, the operation of dewatering the solids cake between (h) and (j) is shorter than in the processing cycle, VZ1 between (c) and (d), with the consequence that the conductivity or residual moisture of the solids cake is higher.

The residual moisture of the discharged solids cake can be checked offline on the basis of a sample of solid matter and compared with the measuring signal at the time of the skimming discharge operation at (d) and (j).

We claim:

1. A device for determining the residual liquid content of solids cakes in a rotating basket of a centrifuge, said device comprising:
   at least two electrodes as sensors, disposed to protrude, spaced apart from each other, through a wall of said rotating basket and into a solids cake which accumulates in said basket during operation;
   a conductivity or capacitance measuring device (13) connected to the electrode sensors to measure the conductivity of the solids cake between said sensors and to determine the residual liquid content thereby; and
   evaluation and control units positioned apart from said basket and configured to contactlessly receive data from said measuring device and, in response thereto, affect the operation of the centrifuge.

2. The device as claimed in claim 1, wherein the basket comprises a basket shell, containing a screen area, a basket base and an edge, and the electrodes are provided in the edge of the basket.

3. The device as claimed in claim 1, wherein the measuring device is provided in the edge of the basket.

4. The device as claimed in claim 1, the electrodes are of a material selected from the group consisting of stainless steel, platinum, gold, nickel and copper.

5. The device as claimed in claim 1, wherein the measuring device is connected to a telemetry unit (14), which transmits measuring data contactlessly from the centrifuge basket (1) to a receiver.

6. The device as claimed in claim 5, wherein the basket of the centrifuge is mounted in a centrifuge housing, and the receiver is provided on the inside of the centrifuge housing.

7. The device as claimed in claim 6, wherein the receiver is connected to said evaluation and control units for controlling the operation of the centrifuge.

8. The device as claimed in claim 1, wherein the measuring device is operated by an external voltage supply, arranged partly outside the centrifuge basket.

9. The device as claimed in claim 8, wherein the voltage supply comprises a high-frequency transmitter with a transmitting coil and an AC/DC converter with a receiver coil, the AC/DC converter being electrically connected to the measuring device.

10. The device as claimed in claim 8, wherein the voltage supply, the measuring device and a telemetry unit which transmits measuring data contactlessly from the centrifuge basket to a receiver are arranged in a ring, closed from the surroundings, which ring is comprised of a non-metallic material.

11. The device as claimed in claim 10, wherein the non-metallic material is a curable plastic.

12. The device as claimed in claim 11, wherein said curable plastic is an epoxy resin or a phenolic resin.

13. The device as claimed in claim 10, wherein the basket comprises a basket shell, containing a screen area, a basket base and a basket edge, and an additional supporting ring is provided around the outer circumference of the ring and is connected to the basket edge.

14. The device as claimed in claim 10, wherein said non-metallic material is a glass-fiber reinforced plastic.

15. A skimming centrifuge, filter centrifuge, centrifugal dryer or screen centrifuge comprising a measuring device according to claim 1.

* * * * *